US009907865B2

(12) United States Patent
Hadimani et al.

(10) Patent No.: US 9,907,865 B2
(45) Date of Patent: Mar. 6, 2018

(54) ROOM TEMPERATURE FERROMAGNETIC GADOLINIUM SILICIDE NANOPARTICLES

(71) Applicants: Magundappa Ravi L. Hadimani, Glen Allen, VA (US); Shalabh Gupta, Ames, IA (US); Shane Harstad, Rockford, MN (US); Vitalij Pecharsky, Ames, IA (US); David C. Jiles, Ames, IA (US)

(72) Inventors: Magundappa Ravi L. Hadimani, Glen Allen, VA (US); Shalabh Gupta, Ames, IA (US); Shane Harstad, Rockford, MN (US); Vitalij Pecharsky, Ames, IA (US); David C. Jiles, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/332,940

(22) Filed: Oct. 24, 2016

(65) Prior Publication Data
US 2017/0119909 A1     May 4, 2017

Related U.S. Application Data

(60) Provisional application No. 62/250,726, filed on Nov. 4, 2015.

(51) Int. Cl.
*A61K 49/06*    (2006.01)
*C01B 33/06*    (2006.01)
*A61K 49/18*    (2006.01)

(52) U.S. Cl.
CPC .......... *A61K 49/06* (2013.01); *A61K 49/1818* (2013.01); *C01B 33/06* (2013.01); *C01P 2004/61* (2013.01); *C01P 2004/62* (2013.01); *C01P 2006/42* (2013.01)

(58) Field of Classification Search
CPC .................................................... C01B 33/06
See application file for complete search history.

(56) References Cited

PUBLICATIONS

R.L. Hadimani et al.; "Growth and characterization of Pt-protected $Gd_5Si_4$ thin films"; Journal of Applied Physics vol. 115; AIP Publishing LLC; Feb. 10, 2014; pp. 17C113-1 to 17C113-3; Ames, Iowa.

(Continued)

*Primary Examiner* — Alexandre F Ferre
(74) *Attorney, Agent, or Firm* — Reinhart Boerner Van Deuren P.C.

(57) ABSTRACT

A particle usable as $T_1$ and $T_2$ contrast agents is provided. The particle is a gadolinium silicide ($Gd_5Si_4$) particle that is ferromagnetic at temperatures up to 290 K and is less than 2 μm in diameter. An MRI contrast agent that includes a plurality of gadolinium silicide ($Gd_5Si_4$) particles that are less than 1 μm in diameter is also provided. A method for creating gadolinium silicide ($Gd_5Si_4$) particles is also provided. The method includes the steps of providing a $Gd_5Si_4$ bulk alloy; grinding the $Gd_5Si_4$ bulk alloy into a powder; and milling the $Gd_5Si_4$ bulk alloy powder for a time of approximately 20 minutes or less.

19 Claims, 3 Drawing Sheets

(56) References Cited

PUBLICATIONS

Hyon Bin Na et al.; "Inorganic Nanoparticles for MRI Contrast Agents"; Advanced Materials vol. 21; Wiley-VCH Verlag GmbH & Co. KGaA; 2009; pp. 2133-2148; Weinheim, Germany.

Nikolai V. Tarasenko et al.; "Laser-aided Preparation and Modification of Gadolinium Silicide Nanoparticles in Liquid"; The Journal of Physical Chemistry; American Chemical Society; 2012; pp. 3897-3902, Minsk, Belarus.

A.L. Pires et al.; "Influence of short time milling in $R_5(Si,G_e)_4$, R=Gd and Tb, magnetocaloric materials"; Institute of Nanoscience and Nanotechnology in Portugal, Centro de Fisica Nuclear da Universidade de Lisboa in Portugal, and Blackett Laboratory in London; date not indicated.

Gustav J. Strijkers et al.; "MRI Contrast Agents: Current status and Future Perspectives"; Anti-Cancer agents in Medicinal Chemistry vol. 7; Jun. 2007; pp. 291-305; The Netherlands.

ROOM TEMPERATURE FERROMAGNETIC GADOLINIUM SILICIDE NANOPARTICLES

CROSS-REFERENCE TO RELATED PATENT APPLICATION

This patent application claims the benefit of U.S. Provisional Patent Application No. 62/250,726, filed Nov. 4, 2015, the entire teachings and disclosure of which are incorporated herein by reference thereto.

STATEMENT REGARDING FEDERALLY SPONSORED RESEARCH AND DEVELOPMENT

This invention was made in part with Government support under Grant No. DE-AC02-07CH11358 awarded by the Department of Energy. The Government has certain rights in this invention.

FIELD OF THE INVENTION

This invention generally relates to magnetic materials and in particular to ferromagnetic particles.

BACKGROUND OF THE INVENTION

Magnetic Resonance Imaging (MRI) is a popular tool for performing clinical diagnoses because it is non-invasive and because it can provide information on the anatomy, function, and metabolism of tissues in vivo. The MRI technique uses powerful magnets to align the nuclear magnetic moment of hydrogen atoms (protons) found in water inside the tissue of a human body. The magnetic field aligns the protons along the direction of the magnetic field produced by the MRI scanner. The MRI scanner then emits radio frequency waves to disrupt the alignment of the protons. The protons found in different tissues in the body respond differently to the disruption, and realignment times vary accordingly. The realignment times are referred to as relaxation times $T_1$ and $T_2$. During realignment, the protons will emit their own radio frequency wave. The exact frequency and intensity depends on the relaxation times, and the emitted radio frequencies are sensed by detectors to form the MRI image.

The intrinsic contrast provided by the $T_1$ and $T_2$ relaxation times is often too limited to enable a sensitive and specific diagnosis. For that reason, MRI Contrast Agents are used to reduce the relaxation times, which sharpen the image contrast. Contrast agents are predominantly used to shorten the $T_1$ relaxation time, although $T_2$ contrast agents also exist. The $T_1$ contrast agents usually contain a paramagnetic metal ion, which has been chelated so as to avoid toxicity within the body.

Such chelated paramagnetic metal ions commonly include the gadolinium ion ($Gd^{+3}$). Some commercially available $T_1$ contrast agents of this type include: Gd-DTPA (gadopentetic acid), Gd-DOTA (gadoteric acid), Gd-DTPA-BMA (gadodiamide), and Gd-DO3A (gadoteridol). However, paramagnetic contrast agents only provide a modest decrease in $T_1$ relaxation time. Additionally, the paramagnetic contrast agents only respond weakly to the magnetic field produced by the MRI scanner. Therefore, the signal-to-noise ratio between some tissues, especially between pathological tissue and its surrounding healthy tissue, remains low, making diagnosis based on the produced images difficult. Further, because the paramagnetic contrast agents only respond weakly to the magnetic field of the MRI scanner, the MRI scanner must operate at very high magnetic field levels.

Disclosed herein are embodiments of a ferromagnetic nanoparticle that has great applicability, among other applications, as $T_1$ and $T_2$ MRI Contrast Agents. These particles have a magnetic moment that is greater than ten times that of paramagnetic contrast agents. Also disclosed herein are exemplary methods for producing the particles. These and other advantages of the invention, as well as additional inventive features, will be apparent from the description of the invention provided herein.

BRIEF SUMMARY OF THE INVENTION

In one aspect, a ferromagnetic material is provided. The material is a gadolinium silicide ($Gd_5Si_4$) particle that is ferromagnetic at temperatures up to 290 K and is less than 2 µm in diameter.

In an embodiment of the material, the $Gd_5Si_4$ particle is ferromagnetic at temperatures up to 310 K. In another embodiment, the $Gd_5Si_4$ particle is less than 1 µm in diameter. In still another embodiment, the $Gd_5Si_4$ particle is less than 500 nm in diameter. In a further embodiment, the $Gd_5Si_4$ particle includes 5 wt % or less $Gd_5Si_3$.

In another aspect, an MRI Contrast Agent that includes a plurality of gadolinium silicide ($Gd_5Si_4$) particles that are less than 1 µm in diameter is provided. In a specific embodiment, the $Gd_5Si_4$ particles are ferromagnetic at temperatures up to 310 K.

In a further aspect, a method for creating gadolinium silicide ($Gd_5Si_4$) particles is also provided. The method includes the steps of providing a $Gd_5Si_4$ bulk alloy; grinding the $Gd_5Si_4$ bulk alloy into a powder; and milling the $Gd_5Si_4$ bulk alloy powder for a time of approximately 20 minutes or less.

In an embodiment, the grinding and milling steps are performed in an inert atmosphere. In a specific embodiment, the inert atmosphere is a noble gas atmosphere.

In another specific embodiment, the milling is performed in a ball mill. In a specific embodiment, a mass ratio of milling media to $Gd_5Si_4$ bulk alloy powder of between 2:1 and 10:1 is used during the milling step. In a more specific embodiment, the milling media is stainless steel balls of two sizes are used. In an even more specific embodiment, a first size stainless steel balls has a diameter of 11.1 mm and a second size of stainless steel balls had a diameter of 6.3 mm. In a further specific embodiment, the ratio of the second size of stainless steels balls to the first size of stainless steel balls is 2:1.

In another embodiment, the $Gd_5Si_4$ bulk alloy is a pure, single-phase alloy.

In still another embodiment, the providing a $Gd_5Si_4$ bulk alloy step includes the steps of supplying a stoichiometric quantity of at least 99.9% purity gadolinium metal; supplying a stoichiometric quantity of at least 99.999% purity silicon; melting the gadolinium and silicon together in an inert atmosphere at least once; and cooling the mixture of gadolinium and silicon at a rate fast enough to avoid neighboring phases. In a more specific embodiment, the melting step is performed at least four times. In another specific embodiment, the melting step is performed in an electric arc furnace on a water-cooled copper hearth.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

Figures 1A, 1B:
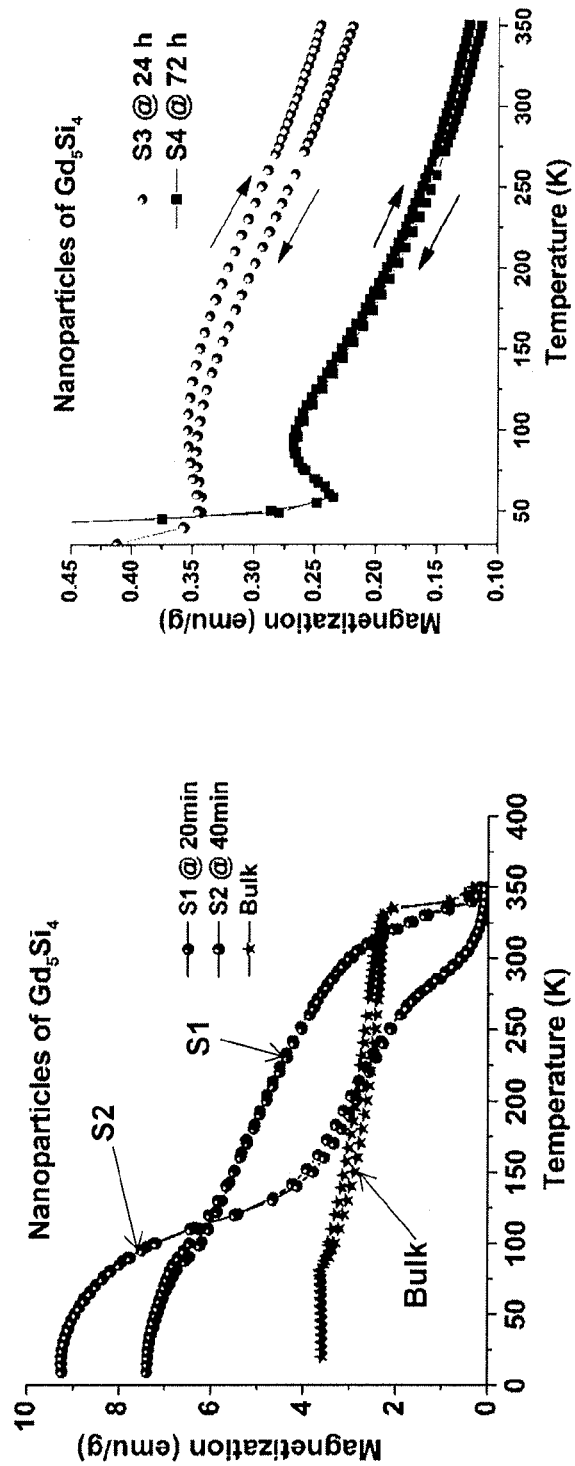
FIGS. 1A-B are graphs showing magnetization as a function of temperature according to an exemplary embodiment of the ferromagnetic particles.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Various embodiments of a ferromagnetic particle of gadolinium silicide ($Gd_5Si_4$) and their applications are provided. Additionally, various methods of creating particles of gadolinium silicide that retain the bulk material's ferromagnetic properties at room temperature are provided. However, as will be recognized by those skilled in the art from the following description, such embodiments are provided by way of example only, not by way of limitation, and that all alternative embodiments are reserved herein.

In general, the gadolinium silicide particles described herein are less than 1 μm in size and are ferromagnetic at human body temperature (approximately 310 K). Indeed, the particles are ferromagnetic up to 350 K, while maintaining about half their magnetization at 325 K. As is known in the art, the ferromagnetic properties of a material are temperature dependent. As temperature increases up to and beyond a critical point (known as the Curie temperature), the material will switch from exhibiting ferromagnetism to paramagnetism. Thus, a benefit of the presently disclosed gadolinium silicide particles is the ability to remain ferromagnetic at human body temperature, especially when used as a contrast agent for use during an MRI.

The ferromagnetic particles are created from a bulk sample through ball milling in an inert atmosphere for approximately 20 minutes. Properties of these ferromagnetic gadolinium silicide particles produced according to the disclosed methods are shown in FIGS. 1-4. As mentioned, the properties of these ferromagnetic particles make them useful as MRI Contrast Agents, and the use of the ferromagnetic particles as MRI Contrast Agents will provide an exemplary context under which the advantages of the ferromagnetic particles will be discussed below. Nevertheless, other applications can benefit from these ferromagnetic particles, including transcranial magnetic stimulation, MRI thermometry, hyperthermic cancer treatment, increasing the piezoelectric coefficient of a material, and making nanostructured magnetocaloric materials.

In one embodiment, the particles are created from a bulk alloy of $Gd_5Si_4$. The bulk alloy was prepared by arc melting a stoichiometric mixture of gadolinium and silicon. In other embodiments, the melting step can be performed using an electric arc furnace, an induction furnace, a hearth furnace, or a crucible furnace or via vacuum induction melting. Commercial grade gadolinium (purity of 99.9% by weight with respect to other rare earth elements) and silicon (>99.999%) can be used as the base materials to create the bulk alloy. However, using commercial grade gadolinium will lead to the formation of a small amount of $Gd_5Si_3$ impurities in the predominantly $Gd_5Si_4$ matrix. Nevertheless, the properties of the resulting bulk alloy will not be substantially degraded. In an embodiment, the arc melting is performed on a water-cooled copper hearth under an argon atmosphere. However, helium or other noble or inert gases could also be used to provide the inert atmosphere.

In an embodiment, the bulk alloy is remelted multiple times to ensure homogeneity of the gadolinium and silicon in the bulk sample. In a specific embodiment, the bulk alloy was remelted six times, and after each melt, the bulk alloy was turned over to improve homogeneity of the gadolinium and silicon within the sample. The last melting was finished by shutting off power to the arc, which provided the highest cooling rate so as to avoid the formation of neighboring phases, such as $Gd_5Si_3$ and $GdSi$. In one embodiment, no further heat treatment was performed on the as-cast bulk material; however, additional heat treatment can be performed if neighboring phases or impurities are present so as to ensure a high fraction of the ferromagnetic $Gd_5Si_4$ phase is present in the bulk alloy. Preparation of the bulk sample according to this method resulted in a single-phase, pure alloy.

After preparing the bulk alloy, the $Gd_5Si_4$ bulk alloy was ground into a powder. The powder was sieved to obtain a powder with nearly uniform particle size of 53 microns or smaller. In order to obtain smaller particles, the powder was further reduced using a high-energy ball-mill without the addition of a liquid processing agent. In order to prevent surface oxidation, the ball-milling and all subsequent manipulations were performed in an inert, argon atmosphere. However, helium or other noble or inert gases could also be used to provide the inert atmosphere.

In one embodiment, during milling, 3.625 grams of stainless steel balls were used for every gram of bulk alloy powder. In other embodiments, a milling media to powder ratio of between 2:1 and 10:1 can be used. Also, in other embodiments, different milling media besides stainless steel balls can be utilized to mill the powder. In a particular embodiment, two sizes of stainless-steel balls were used. The first size stainless steel balls had a diameter of 11.1 mm, while the second size of stainless steel balls had a diameter of 6.3 mm. The ratio of the smaller stainless steel balls to the larger stainless steel balls was 2:1. Nevertheless, in other embodiments, a single size of milling media can be used or a larger multitude of milling media sizes can be used. Additionally, the sizes of the milling media can vary to some extent while maintaining the ratio of between 2:1 and 10:1 media to powder ratio, especially depending on the size of the milled particles that is desired. In order to determine the optimal milling time, samples of the powder were taken at various stages of milling time. Thus, samples were taken at 24 hours (S3) and 72 hours (S4).

A separate batch of powder was milled to produce two additional samples. The first sample was prepared according to the ball milling parameters described above. A sample (S1) was withdrawn from the mill after 20 minutes. At that point, the steel balls were replaced with 2.9 mm stainless steel balls at a mass ratio of stainless steel balls to bulk alloy powder of 10:1. The bulk alloy powder was milled for an additional 20 minutes and another sample (S2) was removed at that point. Thus, S2 underwent a two stage-milling procedure, while S1, S3, and S4 underwent a single stage milling procedure. Table I provides sample identification names, milling times, and milling media information for the samples collected.

TABLE I

SAMPLE ID WITH MILLING TIME AND MILLING BALL DESCRIPTION

| Sample ID | Milling Time | Milling balls (number of balls and diameter in mm) |
|---|---|---|
| S1 | 20 minutes | 2 × 11.1 and 4 × 6.3 |
| S2 | 40 minutes | 2 × 11.1, 4 × 6.3 and 2.9 × 40 |
| S3 | 24 hours | 2 × 11.1 and 4 × 6.3 |
| S4 | 72 hours | 2 × 11.1 and 4 × 6.3 |

After milling, the samples were removed from the inert atmosphere. The concerns of oxidation once milling has been completed are minimal since $Gd_2O_3$ has a magnetic transition temperature below 10 K and will be non-magnetic at operational temperatures. Thus, at small volume fractions, $Gd_2O_3$ will not affect the magnetic properties of $Gd_5Si_4$. Other than small amounts of $Gd_2O_3$, S1 and S2 exhibited no apparent contamination from the ball milling. S3 and S4, however, experienced a significant amount of iron contamination (approximately 30 and 44 vol. %, respectively) from the steel balls and the container. Additionally, S3 and S4 exhibited significant agglomerating. The size of the non-agglomerated particles across all the samples was between 200 nm and 2 μm. The average particle size increased with increased milling time such that S1 had the smallest average particle size followed by S2, S3, and S4, respectively.

FIG. 1A shows the magnetic properties as a function of temperature for S1 and S2 prepared according to the described method and exposed to a magnetic field of 100 Oe. FIG. 1B shows the magnetic properties as a function of temperature for S3 and S4 prepared according to the described method and exposed to a magnetic field of 100 Oe. The y-axes in FIGS. 1A and 1B are different because of the much stronger magnetization reaction of S1 and S2 compared to S3 and S4. As can be seen FIG. 1A, S1 exhibits superior magnetic properties than even the bulk alloy at temperatures up to approximately 320 K, which is above the temperature of a human body.

Through analysis of the particles, it was determined that the particles lose their crystallinity at some point during milling between 20 and 40 minutes. Thus, S2 contained amorphous particles. FIG. 1A also shows that S2 exhibited two ferromagnetic transitions at approximately 100 K and at approximately 280 K. S1 exhibited a weak transition at approximately 100 K. The transitions at 100 K for S1 and S2 likely resulted from the formation of $Gd_5Si_3$ during milling. More importantly, though, S1 retained a ferromagnetic transition between about 330 K and 340 K. FIG. 1B shows that S3 and S4 exhibited much weaker magnetic responses when exposed to the same conditions as S1 and S2.

Figures 2A, 2B:
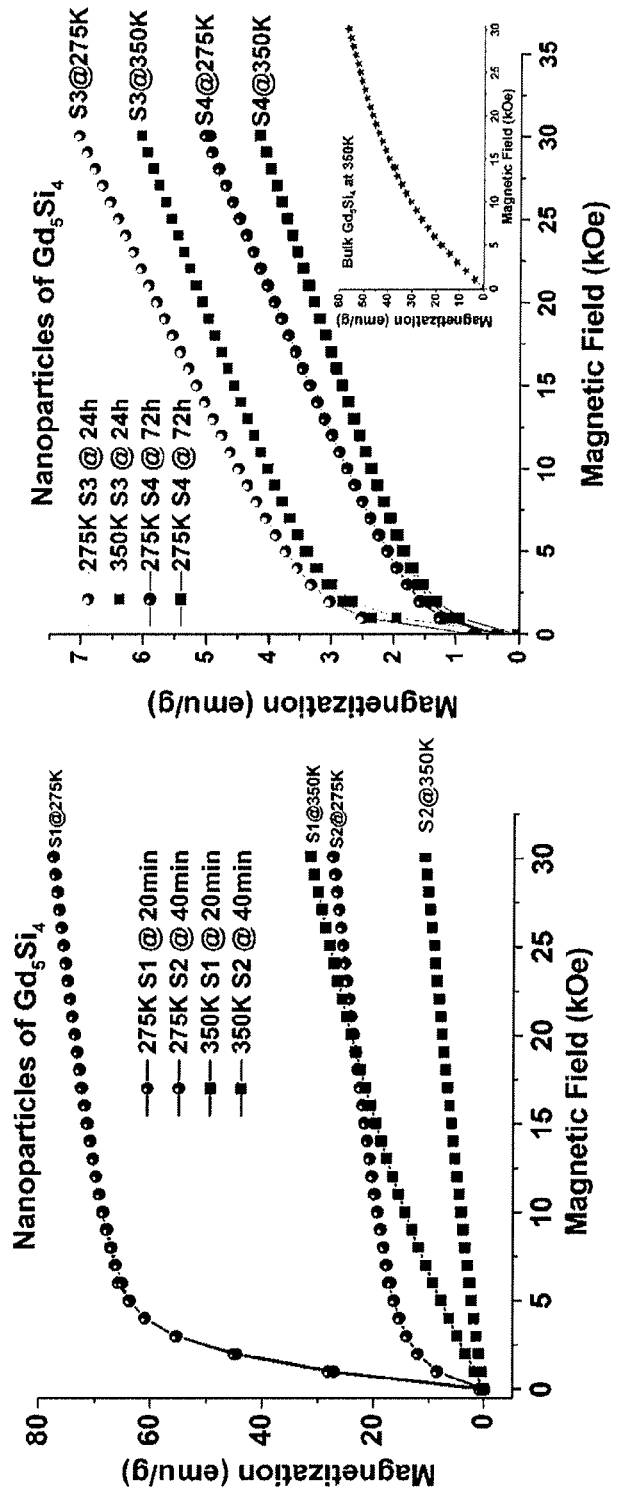
FIGS. 2A-B are graphs showing magnetization as a function of applied magnetic field according to an exemplary embodiment of the ferromagnetic particles.

FIG. 2A shows the magnetic properties as a function of applied magnetic field for S1 and S2 at 275 K and 350 K. FIG. 2B shows the magnetic properties as a function of applied magnetic field for S3 and S4 at 275 K and 350 K. Again, the y-axes of FIGS. 2A and 2B are of different scale because of the much stronger magnetization reaction of S1 and S2 compared to S3 and S4. As can be seen in FIG. 2A, S1 has a much stronger ferromagnetic reaction to the applied magnetic field than S2 at 275 K. At 350 K, both samples display paramagnetic magnetization (i.e., magnetization increases linearly with increasing magnetic field strength). This paramagnetic behavior also demonstrates that neither sample was contaminated with iron during ball milling. Otherwise, the samples would have retained some level of ferromagnetic behavior. By comparison, FIG. 2B shows that S3 and S4 remained ferromagnetic, though at a much weaker level, because of the large amount of iron contamination.

Figure 3:
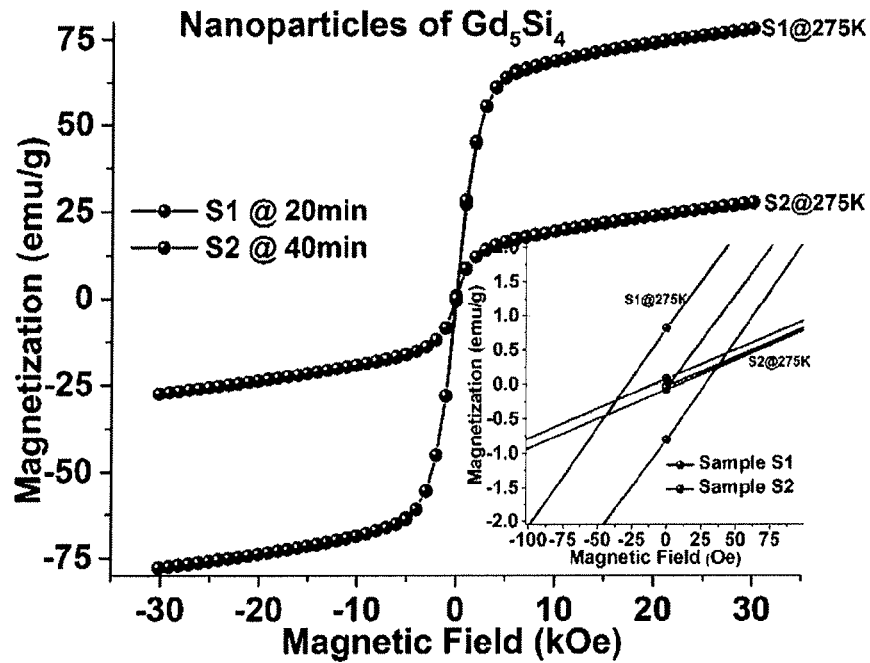
FIG. 3 is a graph of the hysteresis response according to an exemplary embodiment of the ferromagnetic particles.

FIG. 3 shows the hysteresis response of S1 and S2 in a magnetic field varied from −30 kOe to 30 kOe at a temperature of 275 K. The inset graph of FIG. 3 shows the hysteresis response of S1 and S2 in a magnetic field varied from −100 Oe to 100 Oe at a temperature of 275 K. From the graphs shown in FIG. 3, it can be seen that S1 has a much larger amplitude of magnetic response (approximately three times greater at the outer bounds of testing) than S2.

Figure 4:
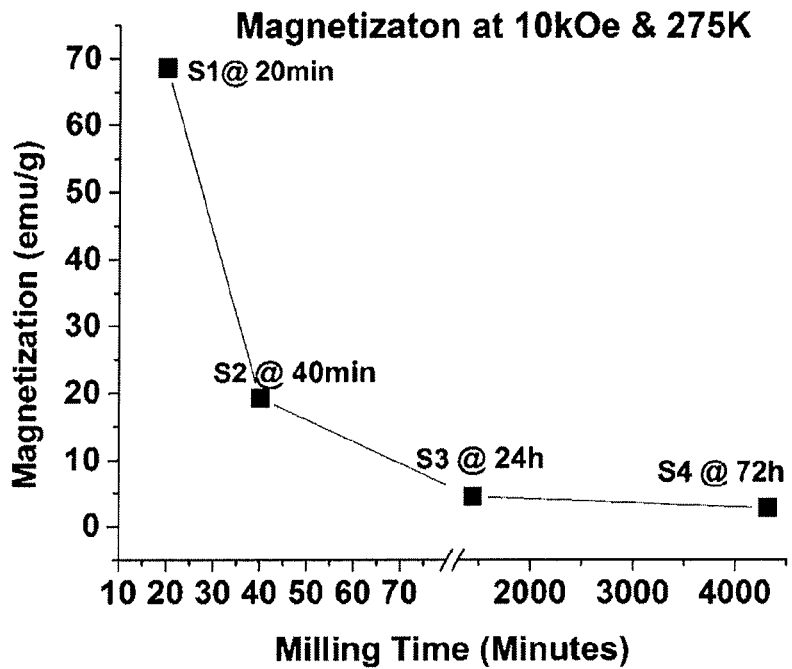
FIG. 4 is a graph of magnetization as a function of milling time according to an exemplary embodiment of the ferromagnetic particles.

FIG. 4 shows the degree of magnetization for S1, S2, S3, and S4 at 10 kOe and 275 K as a function of milling time. As can be seen, the degree of magnetization drops rapidly as milling time increases.

From the samples collected, S1 provided the best combination of magnetic properties and particle size. Thus, in a preferred embodiment, the $Gd_4Si_5$ bulk alloy powder is ball-milled for approximately 20 minutes or less in an inert, argon atmosphere to produce ferromagnetic particles in the size range of 2 μm or smaller.

In one embodiment, the ferromagnetic particles of $Gd_4Si_5$ are incorporated into a saline solution for use as an MRI Contrast Agent. In one embodiment, the concentration of $Gd_4Si_5$ particles in the MRI Contrast Agent solution was between 0.5 and 1.0 mmol/mL. Advantageously, because the shortest milling times produced particles with the best particle size and morphology and because of the relatively small amount of particles needed for use as MRI Contrast Agents, the particles can be produced in small batches in the range of about 1 to 10 kg per batch.

MRI is one of the most widely used techniques to perform non-invasive, accurate, and safe human brain and body imaging because of its high resolution of the various tissue types within a human. In order to provide high resolution images, especially of pathological tissue, large magnets that produce up to 9 Tesla are used to align the protons contained in the water molecules found in a human body. Strong magnets are required because magnetic fields decrease with increasing distance and because magnetic fields are diminished while traveling through a medium.

As discussed above, MRI Contrast Agents are used to improve the signal-to-noise ratio of these images by increasing the magnetic field strength in a patient's body, which decreases the $T_1$ and $T_2$ relaxation time. By decreasing the $T_1$ and $T_2$ relaxation time, the radio frequency wave that is emitted during realignment is more intense. Currently, only paramagnetic or superparamagnetic materials are available for MRI Contrast Agents. Paramagnetic materials are magnetized in response to the magnetic field produced by an MRI scanner. While the magnetic response of the paramagnetic material is linearly proportional to the strength of the applied magnetic field, it is only weakly so. Thus, paramagnetic materials provide only a modest increase in magnetic field strength in the patient's body, which corresponds to a small reduction in $T_1$ relaxation time for the hydrogen atoms.

Ferromagnetic materials, on the other hand, have a high susceptibility to magnetization when subjected to a magnetic field, and therefore, they respond strongly to an applied magnetic field. Accordingly, a ferromagnetic contrast agent would greatly enhance the magnetic field strength in a patient's body, leading to a large reduction in $T_1$ and $T_2$ relaxation time and greater increase in the signal strength of the emitted radio frequency wave. In fact, the ferromagnetic particles discussed herein have more than a ten times greater magnetic moment than paramagnetic contrast agents. By way of comparison, at 310 K, S1 has a magnetization of approximately 2.78 emu/g, while conventional paramagnetic contrast agents exhibit a magnetization of approximately 0.2 emu/g. S2 also exhibits a significantly higher magnetization at room temperature than conventional chelated paramagnetic Gd ions. Thus, using a ferromagnetic contrast agent, the MRI operator could either increase the signal-to-noise ratio of a generated image while operating at the same MRI scanner magnetic field strength or operate a much lower MRI scanner magnetic field strength while maintaining the same signal-to-noise ratio as compared to a paramagnetic MRI Contrast Agent.

Previously, however, preparation of ferromagnetic particles was difficult because ordinary preparation methods destroy the ordered structure required for ferromagnetism. Additionally, ferromagnetic particles could not be reduced to the size necessary for use as MRI Contrast Agents. The ferromagnetic particles created according to the above-described method retain the ferromagnetic properties of the bulk alloy and are sufficiently small for use as MRI Contrast Agents.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A ferromagnetic material, comprising:
   a gadolinium silicide ($Gd_5Si_4$) particle, wherein the $Gd_5Si_4$ particle is ferromagnetic at temperatures up to 290 K and wherein the $Gd_5Si_4$ particle is less than 2 μm in diameter.

2. The material according to claim 1, wherein the $Gd_5Si_4$ particle remains ferromagnetic at temperatures up to 310 K.

3. The material according to claim 1, wherein the $Gd_5Si_4$ particle is less than 1 μm in diameter.

4. The material according to claim 1, wherein the $Gd_5Si_4$ particle is less than 500 nm in diameter.

5. The material according to claim 1, wherein the $Gd_5Si_4$ particle includes 5 wt % or less $Gd_5Si_3$.

6. An MRI contrast agent, wherein the MRI contrast agent comprises:
   a plurality of gadolinium silicide ($Gd_5Si_4$) particles, wherein the $Gd_5Si_4$ particles are less than 1 μm in diameter wherein the $Gd_5Si_4$ particles are ferromagnetic at temperatures up to 290 K.

7. The MRI contrast agent according to claim 6, wherein the $Gd_5Si_4$ particles are ferromagnetic at temperatures up to 310 K.

8. A method for creating the ferromagnetic material of claim 1 comprising the steps of:
   providing a $Gd_5Si_4$ bulk alloy;
   grinding the $Gd_5Si_4$ bulk alloy into a $Gd_5Si_4$ bulk alloy powder; and
   milling the $Gd_5Si_4$ bulk alloy powder for a time of approximately 20 minutes or less.

9. The method of claim 8, wherein the grinding and milling steps further comprise using an inert atmosphere.

10. The method of claim 8, wherein the using an inert atmosphere step further comprises using a noble gas atmosphere.

11. The method of claim 8, wherein the milling step further comprises ball milling.

12. The method of claim 11, wherein the ball milling step further comprises using a milling media with a mass ratio of milling media to $Gd_5Si_4$ bulk alloy powder of between 2:1 and 10:1.

13. The method of claim 12, wherein the using a milling media step further comprises using stainless steel balls having two different sizes.

14. The method of claim 13, wherein the step of using stainless steel balls having two different sizes further comprises using a first size stainless steel balls with a diameter of 11.1 mm and using a second size of stainless steel balls with a diameter of 6.3 mm.

15. The method of claim 14, further comprising the step of providing a ratio of the second size of stainless steels balls to the first size of stainless steel balls of 2:1.

16. The method of claim 8, wherein the step of providing a $Gd_5Si_4$ bulk alloy further comprises providing a pure phase alloy.

17. The method of claim 8, wherein the providing a $Gd_5Si_4$ bulk alloy step further comprises the steps of:
   supplying a stoichiometric quantity of at least 99.9% purity gadolinium metal;
   supplying a stoichiometric quantity of at least 99.999% purity silicon;
   melting the gadolinium and silicon together in an inert atmosphere at least once; and cooling the mixture of gadolinium and silicon at a rate fast enough to avoid neighboring phases.

18. The method of claim 17, wherein the melting step is performed at least four times.

19. The method of claim 17, wherein the melting step further comprises using an electric arc furnace on a water-cooled copper hearth to melt the gadolinium and silicon.

* * * * *